US010413636B2

(12) United States Patent
Pedrozo et al.

(10) Patent No.: US 10,413,636 B2
(45) Date of Patent: Sep. 17, 2019

(54) TISSUE SCAFFOLDS

(75) Inventors: Hugo Pedrozo, Austin, TX (US);
Edward S. Griffey, Fair Oaks Ranch, TX (US); Christopher R. Kaufmann, San Antonio, TX (US)

(73) Assignee: KCI LICENSING, INC., San Antonio, TX (US)

( * ) Notice: Subject to any disclaimer, the term of this patent is extended or adjusted under 35 U.S.C. 154(b) by 1188 days.

(21) Appl. No.: 12/540,489

(22) Filed: Aug. 13, 2009

(65) Prior Publication Data

US 2010/0040687 A1 Feb. 18, 2010

Related U.S. Application Data

(60) Provisional application No. 61/189,097, filed on Aug. 14, 2008.

(51) Int. Cl.
*A61L 27/56* (2006.01)
*A61L 27/36* (2006.01)

(52) U.S. Cl.
CPC ......... *A61L 27/3683* (2013.01); *A61L 27/362* (2013.01); *A61L 27/3633* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 4,233,969 A | 11/1980 | Lock et al. | |
| 4,373,519 A | 2/1983 | Errede et al. | |
| 4,569,348 A | 2/1986 | Hasslinger | |
| 4,703,108 A * | 10/1987 | Silver et al. | ................... 530/356 |
| 5,149,331 A | 9/1992 | Ferdman et al. | |
| 5,263,971 A | 11/1993 | Hirshowitz et al. | |
| 5,298,015 A | 3/1994 | Komatsuzaki et al. | |
| 5,336,616 A | 8/1994 | Livesey et al. | |
| 5,364,756 A | 11/1994 | Livesey et al. | |
| 5,437,651 A | 8/1995 | Todd et al. | |
| 5,549,584 A | 8/1996 | Gross | |
| 5,636,643 A | 6/1997 | Argenta et al. | |
| 5,645,081 A | 7/1997 | Argenta et al. | |
| 5,993,844 A * | 11/1999 | Abraham et al. | ............. 424/423 |
| 6,071,267 A | 6/2000 | Zamierowski | |
| 6,135,116 A | 10/2000 | Vogel et al. | |
| 6,345,623 B1 | 2/2002 | Heaton et al. | |
| 6,553,998 B2 | 4/2003 | Heaton et al. | |
| 6,814,079 B2 | 11/2004 | Heaton et al. | |
| 6,933,326 B1 | 8/2005 | Griffey et al. | |
| 7,198,046 B1 | 4/2007 | Argenta et al. | |
| 7,498,040 B2 | 3/2009 | Masinaei et al. | |
| 7,498,041 B2 | 3/2009 | Masinaei et al. | |
| 7,498,412 B2 * | 3/2009 | Huang | ................... A61L 27/24 424/444 |
| 2002/0120185 A1 | 8/2002 | Johnson | |
| 2003/0035843 A1 | 2/2003 | Livesey et al. | |
| 2003/0036636 A1 | 2/2003 | Huang et al. | |
| 2003/0143207 A1 | 7/2003 | Livesey et al. | |
| 2004/0028738 A1 | 2/2004 | Huang et al. | |
| 2005/0028228 A1 | 2/2005 | McQuillan et al. | |
| 2005/0043819 A1 | 2/2005 | Schmidt et al. | |
| 2005/0159822 A1 | 7/2005 | Griffey et al. | |
| 2005/0260612 A1 * | 11/2005 | Padmini | .................... A61F 2/08 435/6.14 |
| 2006/0073592 A1 | 4/2006 | Sun et al. | |
| 2006/0127375 A1 | 6/2006 | Livesey et al. | |
| 2006/0149040 A1 * | 7/2006 | Snowden | ...................... 530/356 |
| 2006/0210960 A1 | 9/2006 | Livesey et al. | |
| 2007/0219471 A1 | 9/2007 | Johnson et al. | |
| 2007/0248575 A1 | 10/2007 | Connor et al. | |
| 2008/0027542 A1 | 1/2008 | McQuillan et al. | |
| 2009/0035289 A1 | 2/2009 | Wagner et al. | |

FOREIGN PATENT DOCUMENTS

| | | | | |
|---|---|---|---|---|
| WO | WO 90/00060 | * | 1/1990 | ............. A61K 37/12 |
| WO | WO 2002/40630 | | 5/2002 | |
| WO | WO-2009/155600 A2 | | 12/2009 | |

OTHER PUBLICATIONS

Wu et al., Chinese Medical Journal, 2003, 116: 419-423.*
Ju et al., J. Biomed. Mater. Res. Part B: Applied Biomater., online Oct. 31, 2007, 85B: 252-260.*
O'Brien et al., Biomaterials, 2005, 26: 433-441.*
Dagalakis et al., J Biomed Mater Res, 1980, 14: 511-528.*
Smyth et al., Statistical Application in Genetics and Molecular Biology, 20010, 9: 1-12.*
Cao et al.,Tissue Engineering, 2003, 9: S103-S111.*
Leitinger, Annu. Rev. Cell Dev, Biol., 2011, 27: 265-290.*
Vogel, Eur. J. Dermatol., 2001, 11: 506-511; Abstract.*
Madan , Organic Reaction, Conversion, Mechanisms and Problems, 2001.*
Partial International Search for PCT/US2009/053667 dated Jun. 17, 2010, from the European Patent Office.
Argenta, L.C. et al. "Vacuum-Assisted Closure: A New Method for Wound Control and Treatment: Clinical Experience" Annals of Plastic Surgery, vol. 38, No. 6, Jun. 1997; pp. 563-577.
Blackburn II, J.H. et al. "Negative-Pressure Dressings as a Bolster for Skin Grafts" Annals of Plastic Surgery, vol. 40, No. 5, May 1998, pp. 453-457.
Chariker, M.E. et al. "Effective management of incisional and cutaneous fistulae with closed suction wound drainage" Contemporary Surgery, vol. 34, Jun. 1989, pp. 59-63.
Chinn, S.D. et al. "Closed Wound Suction Drainage" The Journal of Foot Surgery, vol. 24, No. 1, 1985; pp. 76-81.
Dattilo Jr., P.P. et al. "Medical Textiles: Application of an Absorbable Barbed Bi-directional Surgical Suture" Journal of Textile and Apparel, Technology and Management, vol. 2, Issue 2, Spring 2002, pp. 1-5.

(Continued)

*Primary Examiner* — Ileana Popa
(74) *Attorney, Agent, or Firm* — McCarter & English, LLP (57) ABSTRACT

Tissue scaffolds are described herein. Also described are devices for treating wounds and methods of treating wounds using tissue scaffolds.

18 Claims, 8 Drawing Sheets

(56) References Cited

OTHER PUBLICATIONS

Defranzo, A.J. et al. "Vacuum-Assisted Closure for the Treatment of Abdominal Wounds" Clinics in Plastic Surgery, vol. 33, No. 2, Apr. 2006, pp. 213-224.

Flack, S. et al. "An economic evaluation of VAC therapy compared with wound dressings in the treatment of diabetic foot ulcers" J. Wound Care, vol. 17, No. 2, Feb. 2008, pp. 71-78.

Griffey, S. et al. "Particulate Dermal Matrix as an Injectable Soft Tissue Replacement Material" J. Biomed. Mater. Res. (Appl. Biomater) vol. 58, 2001, pp. 10-15.

KCI Licensing, Inc. "V.A.C.® Therapy Safety Information" 2007, pp. 1-4.

Masters, J. "Reliable, Inexpensive and Simple Suction Dressings" Letters to the Editor, British Journal of Plastic Surgery, vol. 51, No. 3, 1998, p. 267.

O'Connor, J. et al. "Vacuum-Assisted Closure for the Treatment of Complex Chest Wounds" Ann. Thorac. Surg., vol. 79, 2005, pp. 1196-1200.

International Search and Written Opinion for PCT/US2009/053667 dated Oct. 12, 2010, from the European Patent Office.

Brandi C., et al., "Treatment with vacuum-assisted closure and cryo-preserved homologous de-epidermalised dermis of complex traumas to the lower limbs with loss of substance, and bones and tendons exposure," *Journal of Plastic, Reconstructive and Aesthetic Surgery*, 61(12): 1507-1511 (2008).

Examination Report issued by the European Patent Office for European Application No. 11153969.8 dated Apr. 9, 2013 (3 pages).

Randall K.L., et al., "Use of an Acellular Regenerative Tissue Matrix in Combination with Vacuum-assisted Closure Therapy for Treatment of a Diabetic Foot Wound," *The Journal of Foot & Ankle Surgery*, 47(5): 430-433 (2008).

Wei H-J, et al., "Construction of varying porous structures in acellular bovine pericardia as a tissue-engineering extracellular matrix," *Biomaterials*, 26(14): 1905-1913 (2005).

Yang et al., "A cartilage ECM-derived 3-D porous acellular matrix scaffold for in vivo cartilage tissue engineering with PKH26-labeled chondrogenic bone marrow-derived mesenchymal stem cells," *Biomaterials*, 29(15): 2378-2387 (2008).

Australian Examination Report issued in AU Patent Application No. 2009281937, dated Aug. 5, 2014, 5 pgs.

\* cited by examiner

TISSUE SCAFFOLDS

This application claims priority under 35 U.S.C. § 119 to U.S. Provisional Patent Application No. 61/189,097, which was filed on Aug. 14, 2008.

BACKGROUND

Reduced pressure, or vacuum-assisted, therapies can be effective for improving wound healing due to a variety of different causes and at a number of different anatomical locations. Typically, reduced pressure therapies include a porous material that is placed at a wound site, which aids in the distribution of the reduced pressure. Typical porous materials are sized to fit the wound, and may be periodically replaced with smaller pieces of the porous material as the wound begins to heal and becomes smaller. Typically, a membrane or drape is placed over the porous material to provide an airtight seal at the wound area, and a negative pressure is applied to the porous material to provide a reduced pressure at the wound site.

SUMMARY

According to certain embodiments, a method of processing an acellular tissue matrix for preparing a tissue scaffold is provided. In certain embodiments, a method of preparing a tissue scaffold is provided, comprising adding an acellular tissue matrix to a first aqueous solution of sodium acetate; incubating the first aqueous sodium acetate solution containing the acellular tissue matrix; removing the incubated acellular tissue matrix from the first aqueous sodium acetate solution; treating the incubated acellular tissue matrix with a second aqueous solution of sodium acetate to form a suspension; homogenizing the suspension to form a slurry; cooling the slurry; casting the slurry in a casting container; and lyophilizing the slurry. In certain embodiments, a tissue scaffold comprising an acellular tissue matrix and sodium acetate is provided. In certain embodiments, a wound treatment device comprising a reduced pressure source and a tissue scaffold is provided. In certain embodiments, a tissue scaffold, comprising an acellular tissue matrix that has been processed to have a porosity of between 75% and 90% is provided.

DESCRIPTION OF CERTAIN EXEMPLARY EMBODIMENTS

Reference will now be made in detail to the certain exemplary embodiments according to the present disclosure, certain examples of which are illustrated in the accompanying drawing.

The present disclosure pertains to a method of processing an acelluar tissue matrix for preparing a tissue scaffold. In some embodiments, the tissue scaffold of the present disclosure may be used as part of a wound treatment device that provides reduced pressure therapy. In some embodiments, the physical properties of certain tissue scaffolds such as porosity, strut density, and permeability, may be controlled or altered by adjusting the concentrations, components, and temperatures at which the scaffolds are produced.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit, unless specifically stated otherwise. Also the use of the term "portion" may include part of a moiety or the entire moiety.

The term "acellular tissue matrix," as used herein, refers generally to any tissue matrix that is substantially free of cells and other antigenic material. In various embodiments, acellular tissue matrices derived from human or xenogenic sources may be used to produce the scaffolds. Skin, parts of skin (e.g., dermis), and other tissues such as blood vessels, heart valves, fascia, nerve, or other collagen containing-organ or tissue may be used to create an acellular matrices to produce tissues scaffolds within the scope of the present disclosure.

In certain embodiments, the term "permeability" refers generally to the movement of fluid through a porous medium. In certain embodiments, the specific permeability values of particular tissue scaffolds are calculated by Darcy's Law:

$$k = \frac{Q \cdot l \cdot \mu}{\Delta P \cdot A}$$

where Q equals the total discharge (units of volume per time, e.g., $m^2/s$), (A) is the cross-sectional area to flow, $\Delta P$ is the pressure drop across the system, $\mu$ is the dynamic viscosity (in SI units e.g. kg/(m·s) or Pa's), and (l) is the length over which the pressure drop is taking place over.

Figure 1:
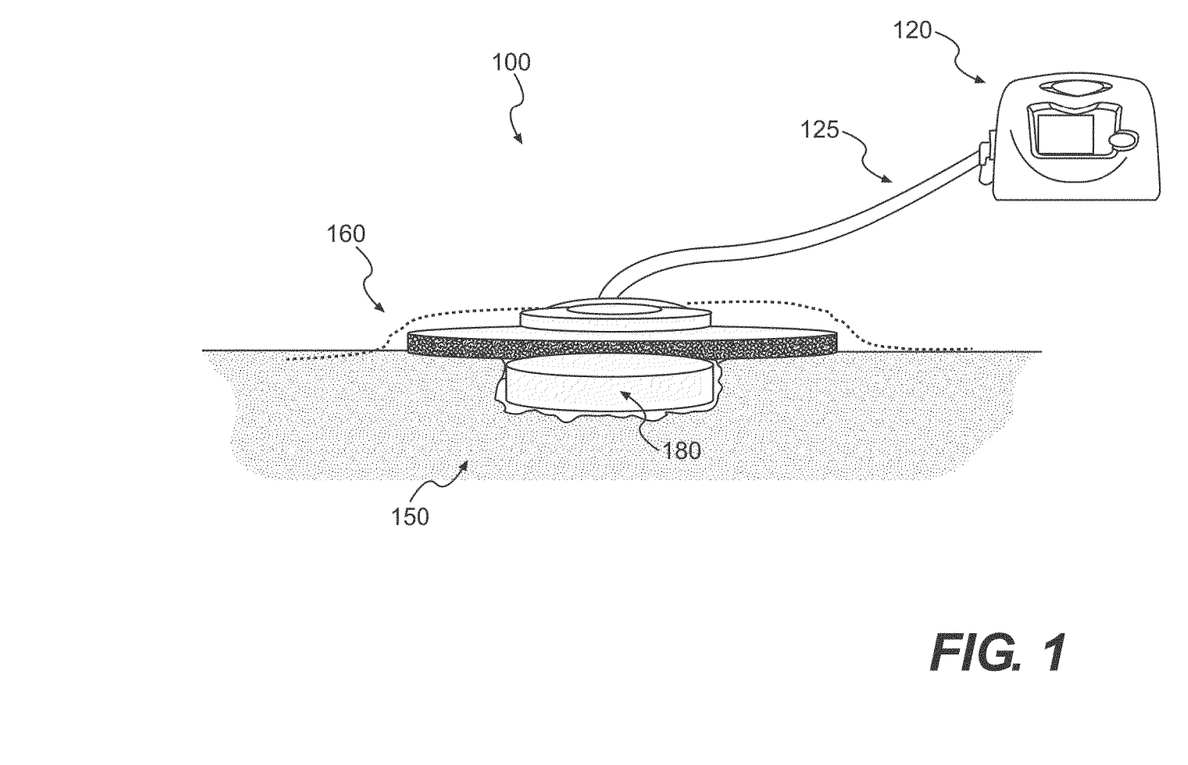
FIG. 1 illustrates a wound treatment device, which provides reduced pressure therapy, according to certain exemplary embodiments.

The term "reduced pressure," as used herein, generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Reduced pressure may initially generate fluid flow in the area of the tissue site and/or a fluid conduit in communication with the tissue site, for example, as shown in FIG. 1. As the hydrostatic pressure around the tissue site approaches the desired reduced pressure, the flow may subside, and the reduced pressure is then maintained. In some embodiments, small amounts of gas can be introduced at intervals to facilitate fluid movement if required. Unless otherwise indicated, values of pressure stated herein are gage pressures.

The term "fluid" as used herein generally refers to a gas or liquid, but may also include any other flowable material, including but not limited to gels, colloids, and foams.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

In various embodiments, devices of the present disclosure can be used for treatment at numerous different anatomical sites. According to various embodiments, tissue scaffolds can be used in a wide array of applications. Certain exemplary applications include, but are not limited to, absorptive dressing, dermal regeneration (for example, for treatments of all types of ulcers and burns), nerve regeneration, cartilage regeneration, connective tissue regeneration or repair (for example, tendon/ligament sleeve), bone regeneration, periodontal applications, wound/foam lining, integrated bandage dressing, substrate/base for skin grafts, vascular regeneration, cosmetic surgery, cosmetic injectable gel, metal and/or polymer implant coating (for example, to increase implant integration and biocompatibility), and replacement of lost tissue (e.g., after trauma, breast reduction, mastectomy, lumpectomy, parotidectomy, or excision of tumors).

FIG. 1 illustrates a wound treatment device 100, including a reduced pressure source 120, according to certain exemplary embodiments. In various embodiments, a variety of reduced pressure therapy devices can be used. For example, suitable reduced pressure therapy devices include V.A.C.® therapy devices produced by Kinetic Concepts, Inc. (San Antonio, Tex.). Such reduced pressure therapy devices can include a vacuum pump that can be fluidly connected to the wound site 150, via a fluid conduit 125 or other fluid connection. Such devices may also include a flexible sheet 160 to cover the wound site 150 and at least partially seal the wound to allow reduced pressure therapy to be provided at the wound site. In addition, such systems may include a tissue scaffold 180, that is placed at the wound site and facilitates wound closure, healing, tissue regeneration or repair, prevents or treats infection, and/or has other beneficial effects. In certain embodiments, the tissue scaffold 180 assists in distributing fluid flow or negative pressure across a site to be treated.

In some embodiments, the flexible sheet 160 will include a flexible polymeric material. In various embodiments, any suitable polymeric material can be selected. In various embodiments, the material does not cause significant irritation, immune response, or heightened risk of infection. In various embodiments, the specific material generally should be of sufficient thickness and impermeability to allow reduced pressure therapy at a wound site under the sheet 160.

In some embodiments, the device 100 will include an adhesive. As used here, and throughout the disclosure, adhesive will be understood to refer to any substance that causes the surfaces of two objects to be attached to one another. In various embodiments, suitable adhesives can include a variety of different cements, glues, resins, or other materials that can facilitate attachment of the flexible sheet 160 to tissue. In some embodiments, the adhesive can include a pressure-sensitive acrylic adhesive. In various embodiments, the adhesives can be applied directly to the structures to be joined, or the adhesives may be applied on tape, or with other supporting substrate materials.

In some embodiments, the adhesive can be applied to a surface of the flexible sheet 160 to attach the sheet to skin or other tissue. In some embodiments, the adhesive will be applied to the surface of the sheet and packaged and/or distributed with the sheet 160. In some embodiments, the adhesive is applied to a surface of the sheet 160 and covered by a non-adhesive material that can be removed to expose the adhesive for use. In certain embodiments, the adhesive can be supplied as a separate component (e.g., in a container or on a tape) that is applied to the sheet 160 to attach the sheet 160 to tissue. In some embodiments, the adhesive can be applied to a patient's skin or other tissue, and the sheet can be applied to the adhesive.

In various embodiments, tissue scaffold 180 can include a variety of suitable materials. For example, a number of different tissue scaffolds will be compatible for use with the above-noted V.A.C.® treatment systems. In some embodiments, the tissue scaffold may comprise a processed acellular tissue matrix. In some embodiments, the acellular tissue matrix may be derived from human skin or from a xenogenic source. In various embodiments, other tissues such as blood vessels, heart valves, fascia, nerve, connective tissue, or other collagen-containing organs or tissues may be used to create a specific acellular matrix within the scope of the present disclosure. In some embodiments, the acellular tissue matrix is an acellular dermal matrix. In various embodiments, the acellular dermal matrix is produced from human dermis or pig dermis. In some embodiments, the methods disclosed herein utilize a dehydrated acellular tissue matrix tissue, such as ALLODERM®, which is commercially available from LifeCell Corporation, Branchburg, N.J. In some embodiments, the methods disclosed herein utilize an acellular tissue matrix tissue, such as STRATTICE™, which is commercially available from LifeCell Corporation, Branchburg, N.J.

Figure 2:
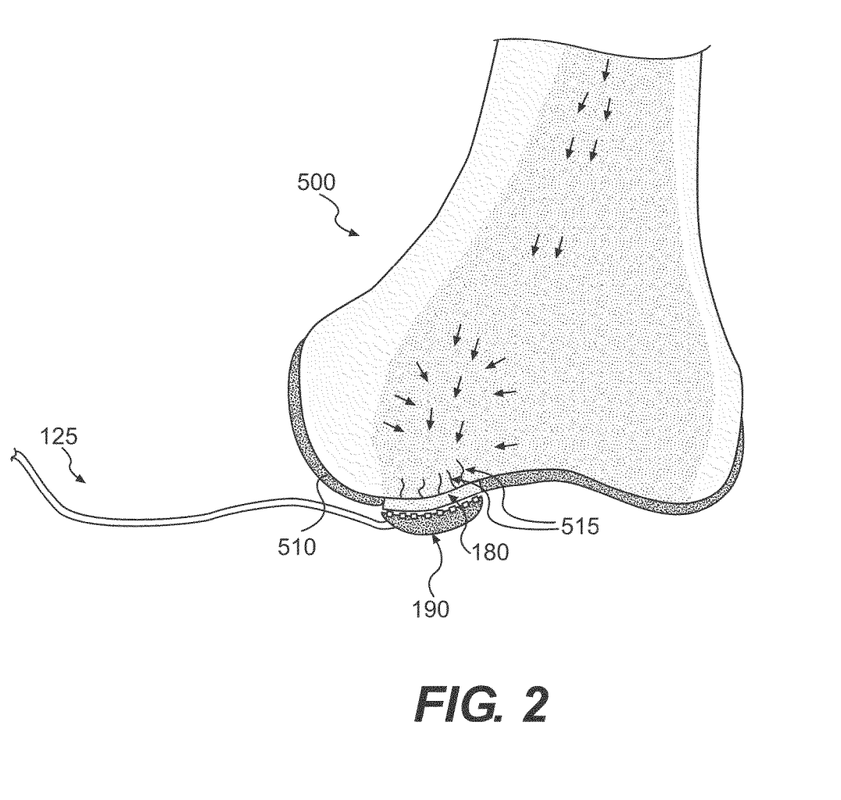
FIG. 2 illustrates a method of treating a cartilage defect using a tissue scaffold, according to certain embodiments.

In various embodiments, acellular tissue matrices can be produced using a variety of different tissue processing techniques. For example, certain exemplary tissue processing techniques for producing acellular tissue matrices are described in U.S. Pat. Nos. 5,336,616 and 5,364,756, both to Livesey et al., in U.S. Pat. No. 6,933,326 to Schiff et al., each of which is incorporated by reference in its entirety. In some embodiments, acellular tissue matrices made from non-human animals can be treated to remove various antigens, or produced from animals genetically modified to lack certain antigens. For example, certain exemplary methods of processing tissues to produce acellular matrices with reduced amounts of or lacking alpha-1,3-galactose moieties, are described in Hui, X. et al., "A Porcine-Derived Acellular Dermal Scaffold that Supports Soft Tissue Regeneration: Removal of Terminal Galactose-α-(1,3)-Galactose and Retention of Matrix Structure," *Tissue Engineering*, Vol. 15, 1-13 (2009), which is incorporated by reference in its entirety FIG. 2 illustrates use of a tissue scaffold to treat a cartilage defect, according to certain embodiments. As shown, a scaffold 180 is used to treat a cartilage defect in a long bone (e.g., femur or humerus). In various embodiments, a scaffold 180 can be used to treat an articular surface or cartilage 510 of any joint. In various embodiments, the tissue scaffold 180 is placed in a defect or excised area of an articular surface or cartilage 510, and a negative pressure is applied to the tissue scaffold 180 through a fluid conduit 125, as described above. In some embodiments, a second material 190 is applied over the tissue scaffold 180, and the second material 190 acts as a manifold to distribute pressure to tissue scaffold 180. In some embodiments, the fluid conduit is in fluid communication with the tissue scaffold 180 without a second material 180.

In some embodiments, the tissue scaffold can be used as a primary treatment method or in connection with another procedure or treatment. For example, in various embodiments, cartilage repair or regeneration can be performed using a technique known in the art as microfracture. As shown in FIG. 2, during a microfracture procedure, a surgeon creates small fractures or openings 515 in bone adjacent to an articular defect. In various instances, the fractures or openings 515 can allow chondrocytes or other cells that can differentiate into chondrocytes to migrate to the articular defect from adjacent bone, bone marrow space, or cartilage. In various instances, these cells can, in turn, help repair or regenerate cartilage.

In some embodiments, after the fractures or openings 515 are produced in the bone 500, the tissue scaffold 180 is placed over the microfracture site, and negative pressure is applied to the scaffold. In some embodiments, the tissue scaffold acts as a manifold to distribute negative pressure over the site to be treated. In some embodiments, the tissue scaffold provides a substrate to support tissue growth, repair, and/or regeneration. In some embodiments, negative pressure is applied to draw cells, growth factors, and/or other biologic elements into the tissue scaffold 180 from the bone 500.

In some embodiments, a method of processing an acellular tissue matrix to produce a tissue scaffold is provided. In some embodiments, the acellular tissue matrix comprises collagen, elastin, and vascular channels. In some embodiments, the acellular tissue matrix is ALLODERM®. In some embodiments, the acellular tissue matrix is STRATTICE™.

In some embodiments, a method for producing a tissue scaffold is provided. In some embodiments, a method comprises adding an acellular tissue matrix to a first aqueous solution of sodium acetate; incubating the first aqueous sodium acetate solution containing the acellular tissue matrix; removing the incubated acellular tissue matrix from the first aqueous sodium acetate solution; treating the incubated acellular tissue matrix with a second aqueous solution of sodium acetate to form a suspension; homogenizing the suspension to form a slurry; cooling the slurry; casting the slurry in a casting container; and lyophilizing the frozen slurry.

In some embodiments, the acellular tissue matrix added to the first aqueous sodium acetate solution is in dehydrated form. In some embodiments, the acellular tissue matrix is cut into small pieces, e.g., cubes, after removal from the first aqueous sodium acetate solution prior to homogenization. In some embodiments, the incubating step takes place at about 4° C. for more than 12 hours.

In some embodiments, the homogenizing step and the cooling step are repeated at least three times. In some embodiments, the homogenizing step is accomplished by a homogenizing Dremmel probe. In some embodiments, the cooling step is accomplished at about 0° C. for about 1.5 minutes or longer. In some embodiments, the casted slurry is frozen at about −70° C. or less for about 2 hours or longer. In some embodiments, the casted slurry is frozen at about −200° C. or less.

In some embodiments, the desired shape and height of the resulting tissue scaffold is determined by the shape and height of the casting container. In some embodiments, the first aqueous sodium acetate solution has a pH of about 3.4, or between about 3.4 and 7.0, or between about 3.4 and 5.0. In some embodiments, the first aqueous solution achieves a final concentration of about 0.1% w/v to about 15% w/v of acellular tissue matrix. In some embodiments, the porosity of the resulting tissue scaffold is from about 75% to about 90%. In some embodiments, the strut density of the resulting tissue scaffold is from about 0.13 g/cm$^3$ to about 0.24 g/cm$^3$. In some embodiments, mechanical strength, porosity, hydration and fluid conductance are controlled by freezing rate, freezing temperature, and the composition of the casting container. In some embodiments, the acellular tissue matrix comprises collagen, elastin, and vascular channels. In some embodiments, the acellular tissue matrix is ALLODERM®. In some embodiments, the acellular tissue matrix comprises collagen, elastin, and vascular channels. In some embodiments, the acellular tissue matrix is STRATTICE™.

In certain embodiments, the tissue scaffold has a desired permeability. For example, the permeability may be selected to allow adequate manifolding or distribution of pressure or flow applied to a wound or therapy site across the site. In certain embodiments, the permeability is controlled by controlling the porosity of the tissue scaffold. In certain embodiments, the permeability is at least $1 \times 10^{-11}$ m$^2$.

In some embodiments, sodium bicarbonate is further added to either one or both of the first or second aqueous sodium acetate solutions, and/or to the slurry. In some embodiments, sodium bicarbonate can be added to the solution just before or during casting. The amount of sodium acetate can be selected to cause foaming of the solution and/or slurry. In certain embodiments, the amount of foaming is selected to control the porosity of all or a portion of a tissue scaffold. In certain embodiments, the slurry is frozen soon after adding sodium acetate to create a desired porosity in the tissue scaffold. In some embodiments, the tissue scaffold can have a porosity that varies across its thickness.

In some embodiments, the tissue scaffold comprises an acellular tissue matrix and sodium acetate. In some embodiments, the tissue scaffold further comprises sodium bicarbonate.

In certain instances, it may be desirable for tissue scaffolds to be resorbed by the body rather than persist for extended periods. In certain instances, tissue scaffolds persist for extended periods, e.g., several months or longer. In certain instances, extended periods provide continued tissue regrowth, remodeling, and regeneration. In certain instances, with some negative pressure wound treatment systems, a material placed over a wound bed is generally replaced periodically (e.g., every few days). In certain instances, replacement of the materials can be painful or damaging to the wound site, especially if granulation tissue has grown into the material. In some embodiments, the tissue scaffolds are bioresorbable. In some embodiments, the tissue scaffolds can be placed in a wound site or implanted, and will be resorbed by the body such that the devices are not removed or replaced.

The following examples demonstrate certain exemplary embodiments of the disclosure. It should be appreciated by those of skill in the art that the techniques disclosed in the examples herein may be modified to achieve similar results.
Preparation of a Tissue Scaffold Aseptically prepared ALLODERM® is cut into strips (approximately 2-3 mm wide) and weighed dry. The desired weight is immersed in the appropriate volume of 20 mM sodium acetate to achieve a final concentration of about 0.1% to about 15.0% w/v (weight of dried material to volume of solution). The strips are then removed from solution, diced into small cubes (approximately 2×2 mm)

using a scalpel, and immersed in a second 20 mM aqueous sodium acetate solution to achieve the desired % w/v. The suspension is then homogenized at full speed using a Dremmel type probe tip for 1 minute, followed by cooling on ice for about 1 minute or longer. The suspension is cooled sufficiently to prevent heating of the suspension to near the melting point of collagen within the suspension during subsequent homogenization, thereby preventing thermal damage to the collagen. The homogenization and cooling steps are repeated three (3) times. The homogenizer tip is then rinsed, and the slurry is then poured into the desired casting containers for the right shape and height. The containers are then covered and placed in a freezer at −70° C. for more than 2 hours to ensure complete freezing. As described below, samples may be frozen at other temperatures to achieve faster freezing, e.g., on liquid nitrogen at about −200° C. The samples are removed from the freezer and placed in a freeze drier. The scaffolds are then removed from the freeze drier upon completion (e.g., about 24 hours or when the temperature of the vessel reaches ambient temperature) of the lyophilization process, and are stored in a dessicator or under vacuum. In some embodiments, sodium bicarbonate can be added to the sample before or after any of the homogenization steps, or just before or during casting.

In various embodiments, freezing rate, freezing temperature, the addition of sodium bicarbonate and the material compositions may all be modified. In certain embodiments, the modifications control the final composition, mechanical strength, hydration, and/or fluid conductance of the resulting tissue scaffold.

EXAMPLE 1

Effect of Scaffold Thickness on Strut Spacing

Figure 3A:
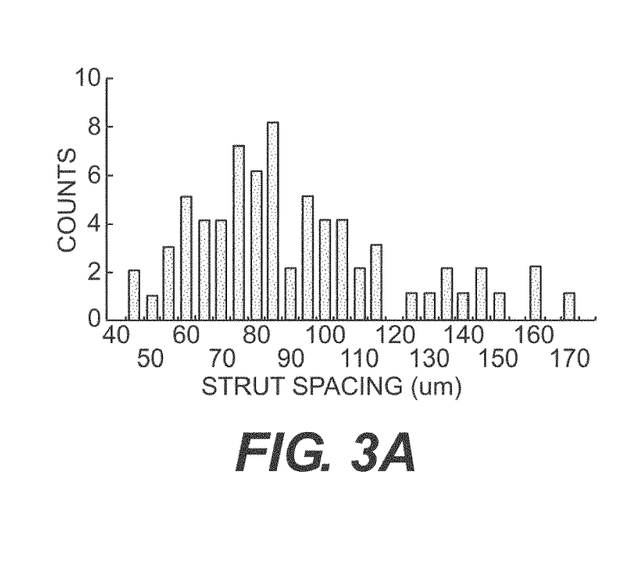
FIGS. 3A-3D are graphs showing the strut spacing for tissue scaffolds, as described in Example 1.
Figure 3B:
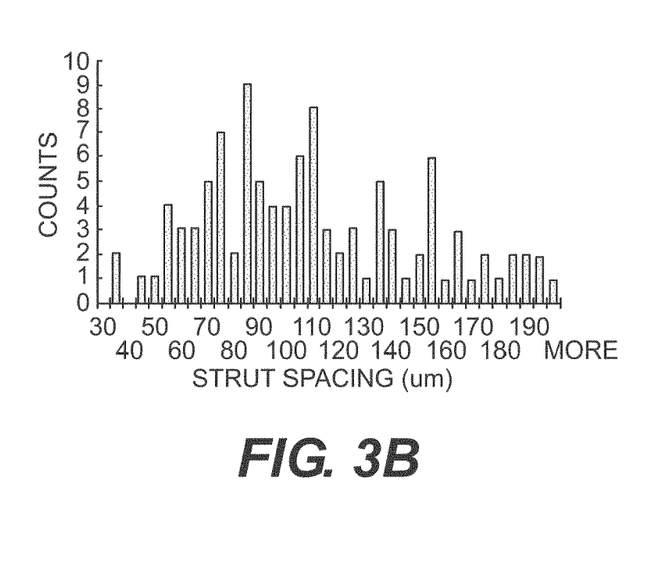
Figure 3C:
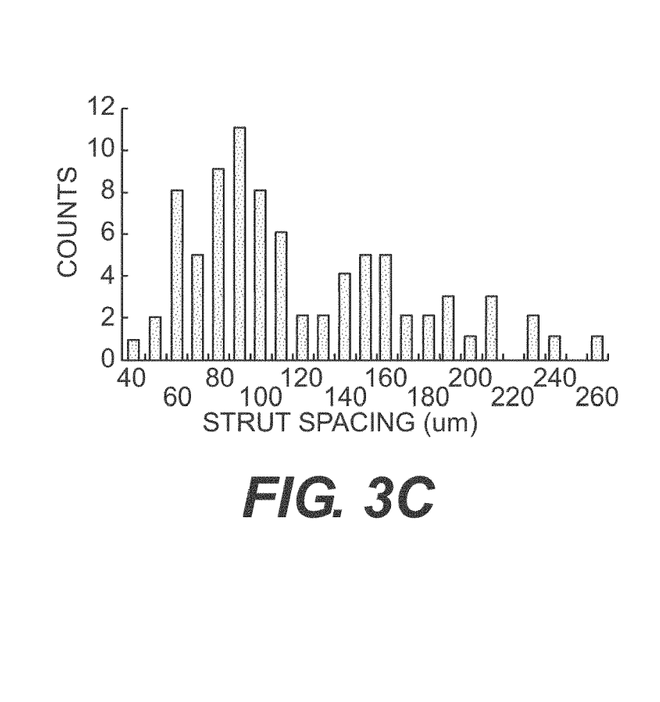
Figure 3D:
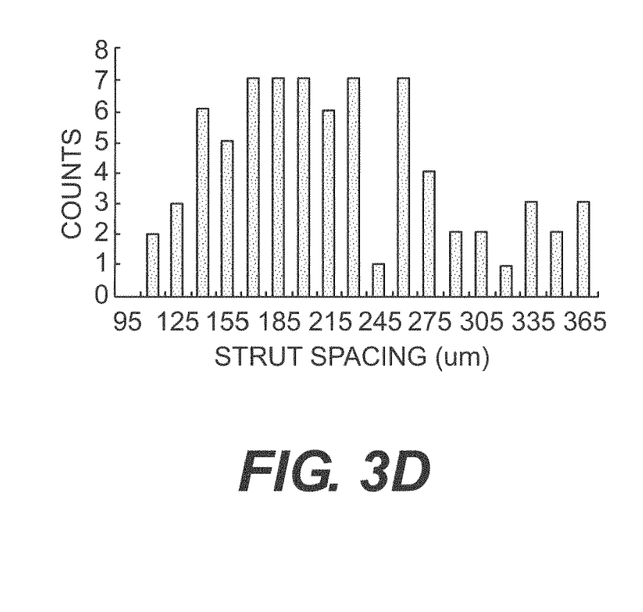

The effect of material thickness on scaffold structure was evaluated. Aseptically prepared ALLODERM® was cut into strips (approximately 2-3 mm wide) and weighed dry. The strips were immersed in the appropriate volume of 20 mM sodium acetate to achieve a final concentration of 5.0% w/v (weight of dried material to volume of solution) and pH of about 3.4. The samples were incubated overnight at 4° C. After incubation overnight, the sample pH rose to about 7.0, and the pH was adjusted back to about 3.4 before further processing. Samples were homogenized three times using a Dremmel type probe to produce a slurry. Samples were cooled on ice for 1 minute between each homogenization step. The samples were casted in six-well culture plates. The wells in which samples were casted had a cylindrical structure with a 35 mm diameter. Samples were cooled at −70° C. for four hours and were then freeze-dried to produce tissue scaffolds. Scaffolds were produced using slurry volumes of 1 ml, 2 ml, 4 ml, and 6 ml. FIGS. 3A-3D are graphs showing the strut spacing for the tissue scaffolds. FIG. 3A represents data for a 1 ml sample, FIG. 3B is date for a 2 ml sample, FIG. 3C is data for a 4 ml sample, and FIG. 3D is data for a 6 ml sample.

As shown in FIGS. 3A-3D, thicker samples resulted in a larger pore size (larger strut spacing) and wider variation pore size. Table 1 provides data including the average pore size, standard deviation, median pore size, and minimum and maximum pore sizes for samples having varying thicknesses. As shown in Table 1, the standard deviation of pore size, range of pore sizes (difference between minimum and maximum pore sizes) and average pore size all increase with increasing material thickness.

TABLE 1

| | Final Volume of NaOAc for Scaffolds Produced with 5% w/v Slurry (material to casting solution) | | | |
|---|---|---|---|---|
| | 1 ml | 2 ml | 4 ml | 6 ml |
| Average Strut Spacing | 89 µm | 108 µm | 133 µm | 212 µm |
| Standard Deviation of Strut Spacing | 29 µm | 41 µm | 51 µm | 67 µm |
| Median Strut Spacing | 83 µm | 101 µm | 97 µm | 202 µm |
| Maximum Strut Spacing | 167 µm | 211 µm | 260 µm | 356 µm |
| Minimum Strut Spacing | 43 µm | 33 µm | 35 µm | 96 µm |

EXAMPLE 2

Effect of Scaffold Composition on Water-Binding Capacity, Porosity, and Permeability In certain embodiments, the ability of tissue scaffolds to bind water can be important for scaffolds remaining hydrated and being effective in supporting tissue repair or regeneration. Sample permeability and water-binding capacity were studied as a function of sample composition (i.e., variation in w/v %). Scaffolds were produced by casting and lyophilizing slurries having varying compositions.

Aseptically prepared ALLODERM® was cut into strips (approximately 2-3 mm wide) and weighed dry. The desired weight of the strips was immersed in the appropriate volume of 20 mM sodium acetate to achieve a final concentrations of 0.1% w/v, 0.5% w/v, 1.0% w/v, 3.0% w/v, 5% w/v, and 8% w/v (each being material weight to sodium acetate solution volume). Each sample pH was about 3.4. Samples were incubated overnight at 4° C. After incubation, the sample pHs rose to about 7.0, and the pHs were adjusted back to about 3.4 before further processing. Samples were homogenized three times using a Dremmel type probe to produce a slurry. Samples were cooled on ice for 1 minute between each homogenization step. Samples were cooled at −70° C. for four hours and were then freeze-dried to produce tissue scaffolds.

Figure 4:
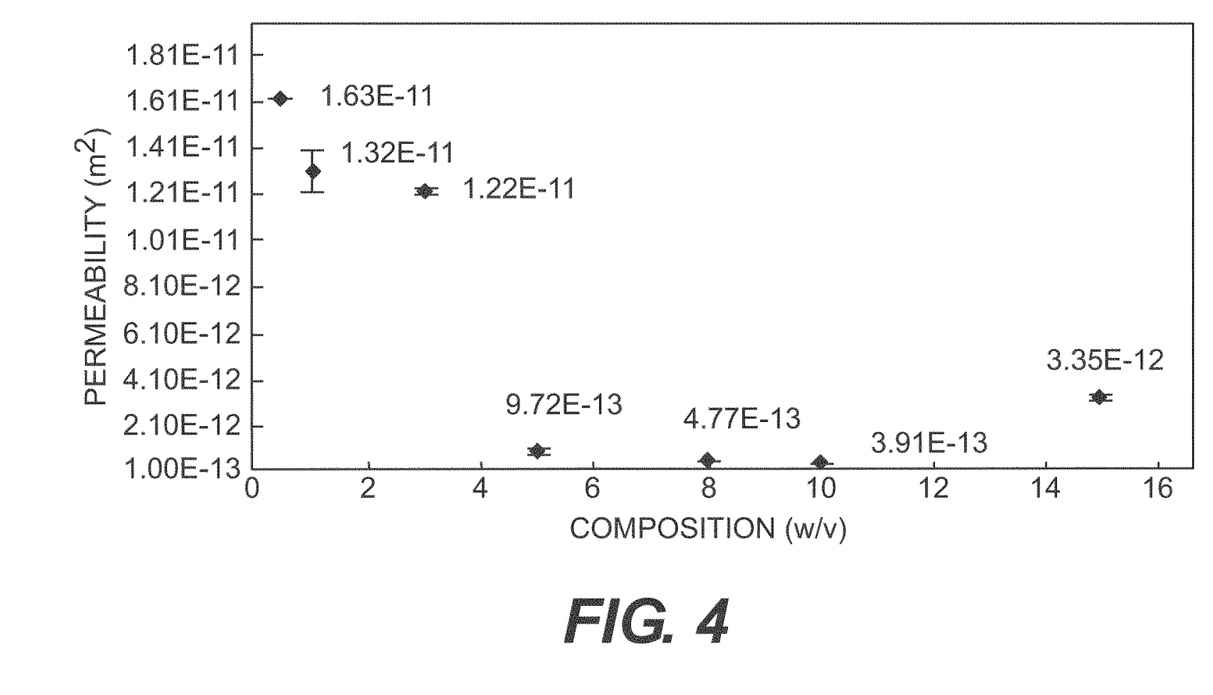
FIG. 4 is a graph showing the permeability versus composition for tissue scaffolds, as described in Example 2.

Table 2 provides data for sample water-binding capacity as a function of sample composition, and FIG. 4 is a graph showing the permeability versus composition for tissue scaffolds. As shown in Table 2 and FIG. 4, as the sample w/v % increased, the sample water-binding capacity increased and sample permeability decreased.

TABLE 2

| Soaking Capacity of Exemplary Tissue Scaffolds | | | | | |
|---|---|---|---|---|---|
| Dry AlloDerm/NaOac (w/v) | Soaking Capcity (g/cm$^3$) | Thickness (% change) | Length (% change) | Breadth (% change) | Volume (% change) |
|---|---|---|---|---|---|
| 0.1% | n/a | −79.2 | 8.5 | 5.6 | −76.1 |
| 0.5% | 0.53 | −42.9 | 1.5 | 1.6 | −41.0 |
| 1.0% | 0.32 | 3.8 | 2.3 | 3.4 | 9.8 |
| 3.0% | 0.56 | 3.6 | 2.4 | 2.6 | 8.8 |
| 5.0% | 0.68 | 7.6 | 6.7 | 4.8 | 20.3 |
| 8.0% | 0.80 | 9.1 | 0.7 | 0.8 | 10.8 |

Table 3 provides data on sample strut density and porosity as a function of sample composition. The sample porosity followed a relatively normal distribution, with sample strut spacing and porosity increasing as sample composition varies from 0.1% to about 5.0%, and decreasing with further increase in sample composition.

TABLE 3

Porosity and Strut Density of Tissue Scaffolds

| Dry AlloDerm/NaOAc (w/v) | Strut Density (g/cm³) | % Porosity |
|---|---|---|
| 0.1% | 0.132 | 89.0 |
| 0.5% | 0.075 | 84.6 |
| 1.0% | 0.154 | 89.9 |
| 4.0% | 0.264 | 88.7 |
| 5.0% | 0.423 | 91.0 |
| 8.0% | 0.486 | 89.2 |
| 10.0% | 0.395 | 84.1 |
| 15.0% | 0.234 | 79.7 |

EXAMPLE 3

Effect of Freezing Rate/Temperature on Scaffold Structure

In some embodiments, it may be desirable to decrease average strut spacing and/or control variation in sample porosity. In some embodiments, these features can be controlled by controlling the temperature at which the sample is cooled and/or the cooling rate.

Aseptically prepared ALLODERM® was cut into strips (approximately 2-3 mm wide) and weighed dry. The strips were immersed in the appropriate volume of 20 mM sodium acetate to achieve a final concentration of 5.0% w/v (weight of dried material to volume of solution) and pH of 3.4. Samples were incubated for about 48 hours at 4° C. After incubation, the sample pH rose to about 7.0, and the pH was adjusted back to about 3.4 before further processing. Samples were homogenized three times using a Dremmel type probe to produce a slurry. Samples were cooled on ice for 1 minute between each homogenization step. The slurry was poured into copper wells. The wells in which samples were casted had a cylindrical structure with a 35 mm diameter. The samples were flash frozen at −200° C. by placing copper wells filled with slurry in liquid nitrogen and then immediately freeze-drying to produce tissue scaffolds.

Figure 5:
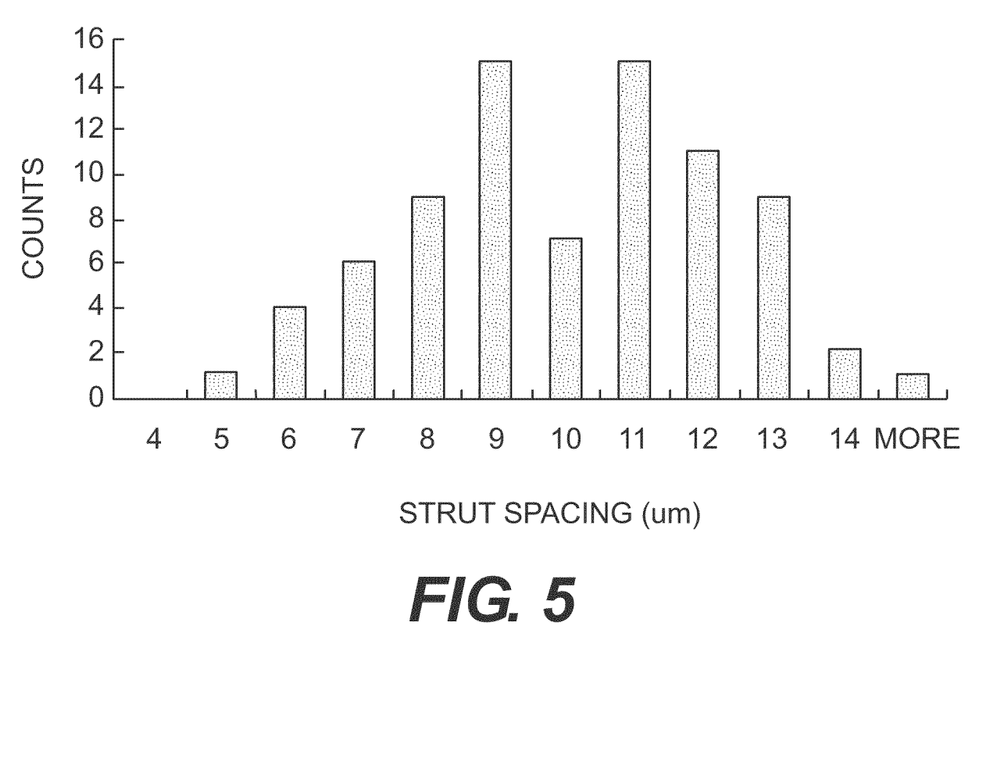
FIG. 5 is a graph showing the strut spacing for a tissue scaffold produced according to certain exemplary embodiments, as described in Example 3.

FIG. 5 shows the strut spacing for tissues produced in this manner, and Table 4 provides data including the average pore size, standard deviation, median pore size, and minimum and maximum pore sizes for samples having varying thicknesses. As shown, the sample had less variation in pore size and smaller average pore size than samples cooled at −70° C., as shown in FIGS. 3A-3D.

TABLE 4

Foam Strut Spacing for Samples Cooled at −200° C.

| Foam Strut Spacing (microns) | |
|---|---|
| Average | 9.5 |
| Standard Deviation | 2.2 |
| Median | 9.7 |
| Maximum | 14.2 |
| Minimum | 4.2 |

EXAMPLE 4

Culture of Isolated Chondrocytes on Tissue Scaffolds

Figure 6A:
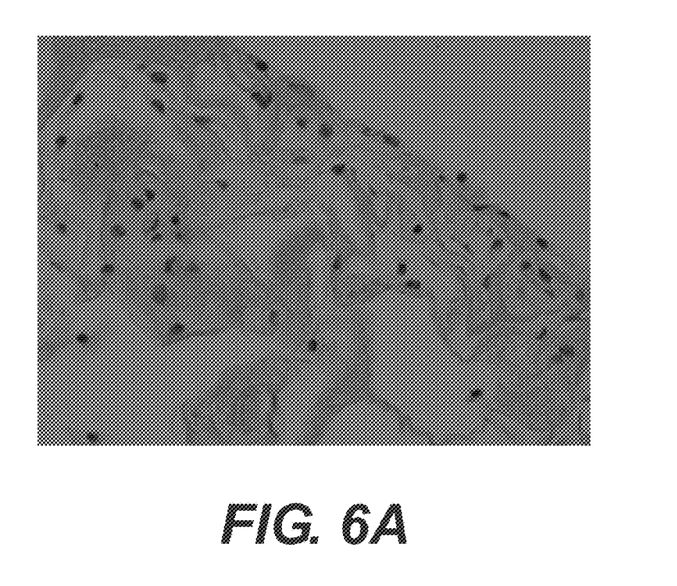
FIGS. 6A-6B are photomicrographs of chondrocytes cultured on tissue scaffolds, as described in Example 4.
Figure 6B:
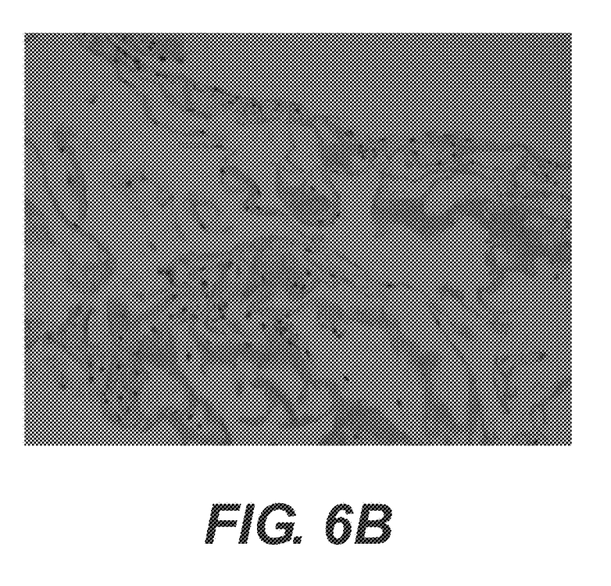
Figure 7A:
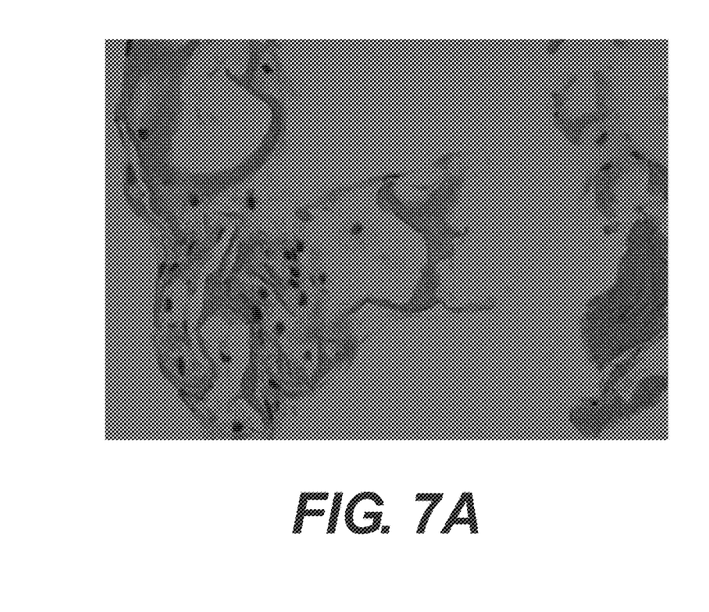
FIGS. 7A-7B are photomicrographs of chondrocytes cultured on tissue scaffolds, as described in Example 4
Figure 7B:
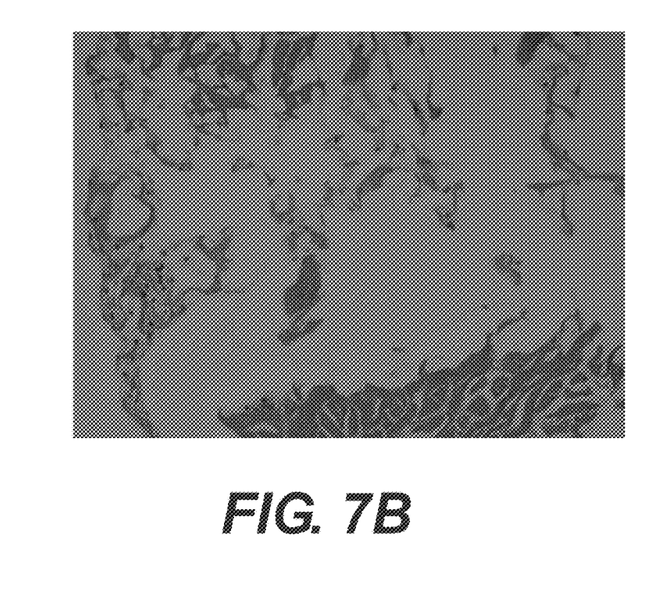

In certain instances, when cultured in typical media, (see Eyrich, D. et al., "Long-term stable fibrin gels for cartilage engineering", *Biomaterials,* 28(1):55-65.(2007)), chondrocytes are known to dedifferentiate into fibroblasts. Therefore, in certain embodiments, tissue scaffolds used for regeneration of cartilage support a continued chondrocyte phenotype when implanted at a treatment site. Certain tissue scaffolds were tested to determine if they support growth of chondrocytes without causing differentiation to fibroblasts. One set of scaffolds was produced using human acellular dermal matrices (ALLODERM®), and a second set was produced using porcine acellular dermal matrices (STRATTICE™). The material was cut into strips (approximately 2-3 mm wide) and weighed dry. The strips were immersed in the appropriate volume of 20 mM sodium acetate to achieve a final concentration of 5.0-8.0% w/v (weight of dried material to volume of solution) and were stored for about 48 hours at 4° C. Samples were homogenized three times using a Dremmel type probe to produce a slurry. Samples were cooled on ice for 1 minute between each homogenization step. The samples were casted in six-well culture plates. The wells in which samples were casted had a cylindrical structure with a 35 mm diameter. Samples were cooled at −70° C. for four hours and were then freeze-dried to produce tissue scaffolds. The scaffolds were seeded with primary sheep articular chondrocytes isolated via an overnight digestion in collagenase, according to standard protocols, The cells were cultured for 14 or 21 days in 10% Fetal Bovine Serum in DMEM at 37° C. and 5% Atmospheric $CO_2$ with 100% humidity FIGS. 6A-6B are photomicrographs of chondrocytes cultured on tissue scaffolds produced with ALLODERM®, and FIGS. 7A-7B are photomicrographs of chondrocytes cultured on tissue scaffolds produced with STRATTICE™. Both human and porcine tissue scaffolds supported chondrocyte growth and infiltration, and grossly appeared to maintain chondrocyte phenotypes.

While systems and methods have been described with reference to tissue growth and healing in human patients, it should be recognized that these systems and methods for applying reduced pressure tissue treatment can be used in any living organism in which it is desired to promote tissue growth or healing. Similarly, the systems and methods may be applied to any tissue, including without limitation bone tissue, adipose tissue, muscle tissue, neural tissue, dermal tissue, vascular tissue, connective tissue, cartilage, tendons, or ligaments. While the healing of soft tissue may be an exemplary focus of applying reduced pressure tissue treatment as described herein, the application of reduced pressure tissue treatment, especially to tissues located beneath a patient's skin, may also be used to generate tissue growth in tissues that are not diseased, defective, or damaged. For example, it may be desired to use the percutaneous implantation techniques to apply reduced pressure tissue treatment to grow additional tissue at a tissue site that can then be harvested. The harvested tissue may be transplanted to another tissue site to replace diseased or damaged tissue, or alternatively the harvested tissue may be transplanted to another patient.

Other embodiments will be apparent to those skilled in the art from consideration of the specification and practice of the devices and methods disclosed herein.

What is claimed is:

1. A method of preparing a tissue scaffold, comprising:
adding an acellular tissue matrix to at least one aqueous solution comprising sodium acetate;
incubating the acellular tissue matrix in the at least one aqueous solution comprising sodium acetate;
mechanically homogenizing the acellular tissue matrix and the at least one aqueous solution comprising sodium acetate to form a slurry containing the acellular tissue matrix;
cooling the slurry;
casting the slurry containing the homogenized acellular tissue matrix in a casting container;
cooling the slurry in an environment of about −70° C. or less to freeze the slurry; and
lyophilizing the slurry to produce a tissue scaffold of acellular tissue matrix having a porosity of about 75% to about 90%.

2. The method of claim 1, wherein the acellular tissue matrix added to the at least one aqueous sodium acetate solution is added in dehydrated form.

3. The method of claim 1, wherein the acellular tissue matrix is cut into small pieces prior to homogenization.

4. The method of claim 1, wherein the incubating takes place at about 4° C. for more than 12 hours.

5. The method of claim 1, wherein the homogenizing and the cooling are repeated at least three times.

6. The method of claim 1, wherein the cooling is accomplished at about 0° C. for about 1.5 minutes or longer.

7. The method of claim 1, wherein the lyophilizing the slurry includes freezing the slurry at −200° C. or less.

8. The method of claim 1, wherein the shape and height of the resulting tissue scaffold are determined by the shape and height of the casting container.

9. The method of claim 1, wherein the at least one aqueous sodium acetate solution has a pH of about 3.4.

10. The method of claim 1, wherein the at least one aqueous sodium acetate solution achieves a final concentration of about 0.1% w/v to about 15% w/v of acellular tissue matrix.

11. The method of claim 1, wherein the resulting tissue scaffold has a strut density from about 0.13 g/cm 3 to about 0.24 g/cm 3.

12. The method according to claim 1, wherein sodium bicarbonate is further added to the at least one aqueous solution comprising sodium acetate.

13. The method of claim 1, wherein mechanical strength, porosity, hydration and fluid conductance of the tissue scaffold are controlled by controlling at least one condition selected from the freezing rate, the freezing temperature, and the composition of the casting container.

14. The method of claim 1, wherein the acellular tissue matrix is a dermal acellular tissue matrix.

15. The method of claim 14, wherein the acellular tissue matrix is a human dermal acellular tissue matrix.

16. The method of claim 14, wherein the acellular tissue matrix is a porcine dermal acellular tissue matrix.

17. The method of claim 1, wherein the acellular tissue matrix comprises collagen, elastin, and vascular channels.

18. A tissue scaffold made by a process comprising:
adding an acellular tissue matrix to at least one aqueous solution comprising sodium acetate;
incubating the acellular tissue matrix in the at least one aqueous solution comprising sodium acetate;
mechanically homogenizing the acellular tissue matrix and the at least one aqueous solution comprising sodium acetate to form a slurry containing the homogenized acellular tissue matrix;
cooling the slurry;
casting the slurry containing the homogenized acellular tissue matrix in a casting container;
cooling the slurry in an environment of about −70° C. or less to freeze the slurry; and
lyophilizing the slurry to produce a tissue scaffold of acellular tissue matrix having a porosity of about 75% to about 90%.

* * * * *